United States Patent
Bächi (10) Patent No.: US 7,521,179 B2
(45) Date of Patent: Apr. 21, 2009

(54) THERMO-OPTICAL ANALYSIS SYSTEM FOR BIOLOGICAL REACTIONS

(75) Inventor: Daniel Bächi, Schübelbach (CH)

(73) Assignees: Lukas Bestmann; Jürg Dual

(*) Notice: Subject to any disclaimer, the term of this patent is extended or adjusted under 35 U.S.C. 154(b) by 328 days.

(21) Appl. No.: 10/485,819

(22) PCT Filed: Aug. 21, 2002

(86) PCT No.: PCT/EP02/09340

§ 371 (c)(1),
(2), (4) Date: Mar. 12, 2004

(87) PCT Pub. No.: WO03/019158

PCT Pub. Date: Mar. 6, 2003

(65) Prior Publication Data

US 2004/0241691 A1 Dec. 2, 2004

(30) Foreign Application Priority Data

Aug. 21, 2001 (CH) .................................. 1544/01

(51) Int. Cl.
*C12Q 1/68* (2006.01)
*C12M 1/36* (2006.01)
*G01N 15/06* (2006.01)

(52) U.S. Cl. ...................... 435/6; 435/283.1; 435/288.4; 435/288.7; 422/68.1; 422/82.05; 422/82.08

(58) Field of Classification Search .................. None
See application file for complete search history.

(56) References Cited

U.S. PATENT DOCUMENTS 4,038,151 A 7/1977 Fadler et al.
5,587,128 A * 12/1996 Wilding et al. ................. 422/50
5,589,136 A 12/1996 Carrano et al.
5,639,423 A 6/1997 White et al.
5,681,484 A 10/1997 Cherukuri et al.
6,369,893 B1 * 4/2002 Christel et al. ............... 356/417
6,379,929 B1 * 4/2002 Burns et al. .................. 435/91.2
7,016,523 B1 * 3/2006 Ogawa .......................... 382/133

FOREIGN PATENT DOCUMENTS

WO WO 99 46045 9/1999
WO WO 02 29397 4/2002

* cited by examiner

*Primary Examiner*—BJ Forman
(74) *Attorney, Agent, or Firm*—Shoemaker and Mattare (57) ABSTRACT

The invention relates to a reaction device, comprising a sample chamber matrix (1), comprising at least two reaction chambers (2) whose walls are permeable with respect to electromagnetic radiation in an area required for fluorescence measurement; at least one opening (3); a heating device (8a); and a temperature measurement device (8b). The invention also relates to a device (G) for carrying out and detecting chemical reactions, comprising at least one light source (24, 25) which emits electromagnetic radiation in an area required for fluorescence measurement, a detection device (28) for the detection of electromagnetic radiation in an area required for fluorescence measurement, said unit (28) being arranged at a right angle to the at least one light source (24, 25); a control unit comprising a central unit for controlling temperature and the at least one light source (24, 25), in addition to receiving and optionally processing a signal from the detection unit (28); an opening (H) for receiving the above-mentioned reaction device (17), said reaction device (R) being able to communicate with the control unit when inserted, being arranged on the plane of the at least one light source (24, 25) below the detection unit (28). The reaction device (R) and the device (G) are suitable for carrying out and evaluating chemical reactions or biochemical reactions such as a polymerase chain reaction.

22 Claims, 10 Drawing Sheets

THERMO-OPTICAL ANALYSIS SYSTEM FOR BIOLOGICAL REACTIONS

The present invention relates to a thermo-optical analysis system which is suitable, in particular, for carrying out and evaluating biochemical reactions.

Many biochemical reactions need to be carried out at a particular temperature in order to obtain an optimum result, or sometimes any result at all. One prominent example is the polymerase chain reaction (PCR). PCR can be used to amplify polynucleotides (such as DNA or RNA) selectively by a factor $10^8$ to $10^9$. This makes it possible to multiply the normally small amounts of DNA or RNA that are present in the reaction mixture taken from an organism, so as to allow detailed determination or analysis of the polynucleotides (for example DNA or RNA).

PCR is described, for example, in U.S. Pat. Nos. 4,683,195, 4,683,202, 4,800,159 and 4,695,188. The principle of PCR may be summarized as follows: a polymerase enzyme for catalyzing the amplification reaction, deoxyribonucleic acid triphosphates (dNTPs) as components of the polynucleotides to be synthesized, oligonucleotide primers for initiating the reaction and optionally other substances, such as buffers, are added to a reaction mixture containing the polynucleotide to be amplified. This reaction mixture is subsequently subjected to a temperature cycle, in which the mixture is brought to a defined temperature for a particular period of time. A conventional temperature cycle consists in first bringing the reaction mixture to a temperature in the range of 90-100° C. for a particular period of time (s to min), then to a temperature in the range of 40-80° C. for a particular period of time, and lastly bringing the mixture to a temperature of about 70-75° C. for a particular period of time. The different temperatures respectively give rise to denaturing of the polynucleotide, binding of the primers that initiate the polymerase reaction, and to the polymerase reaction itself. This temperature cycle is repeated until there is an intended amount of nucleotide in the mixture. Additional steps may be carried out in between, for example in order to purify the polynucleotide. The amplified nucleic acids (for example DNA or RNA) may then be detected by known techniques. A range of methods have been described for this, which are based for example on optical principles such as fluorescence measurement or labeling of the polynucleotide with radioactive substances.

A range of systems have been proposed which can be used for carrying PCR and subsequent analysis of the amplified polynucleotide. The majority of such systems, however, are very large and inefficient since the temperature control is carried out using external energy sources. This entails a considerable energy loss, since a large proportion of the system has to be heated up and cooled. Setting the intended temperature is time-consuming and prone to inaccuracies. In systems which use the ambient temperature for cooling, it may prove very difficult or even impossible to set the system to a temperature of about 25° C. when the ambient temperatures are high.

U.S. Pat. Nos. 5,589,136 and 5,639,423 describe a microreactor for carrying out chemical reactions. This reactor comprises a reaction chamber with an opening, through which a reaction mixture to be amplified can be introduced into the reactor. The reaction chamber is made of doped polysilicon and raw silicon in order to ensure controlled heating and cooling. The reaction chamber furthermore comprises windows made of silicon nitride. A heating device is arranged in the reactor, facing one of these windows. It is described that the detection can be carried out in a corresponding device perpendicular to the light source. This system, however, has a complicated design. In order to simultaneously carry out a plurality of procedures, a plurality of separate reaction chambers need to be introduced into the same reaction and detection device.

U.S. Pat. No. 5,958,349 describes a reaction vessel, for example for PCR. This reaction vessel comprises two large surfaces for rapid thermal transfer. The vessel has a triangular shape overall. Electromagnetic radiation can be sent into the vessel or read out through the smaller surfaces of the vessel.

Multichamber systems for PCR and subsequent detection are known. In the Perkin Elmer 7700 apparatus, the optical excitation of the 96 holes of a microtiter plate is carried out using a single optical fiber. The latter, however, has to be guided using complex mechanical means. In the LightCycler from Roche, a single sample capillary is sequentially subjected to a fluorescence measurement. In this case, the sample capillary needs to be rotated past the excitation and detection unit.

It was therefore an object of the present invention to provide a system for carrying out chemical reactions such as PCR, and/or for detecting proteins, and/or for detecting and antigen/antibody complexes, and for subsequently detecting the reaction product, with the aid of which a plurality of reaction mixtures can be simultaneously processed and evaluated.

This object is achieved according to the invention by a reaction device and an apparatus as claimed in the independent claims.

The system according to the invention for carrying out chemical reactions comprises a reaction device which can be inserted into an apparatus having optical devices and a control unit. The reaction device may be filled with the reaction mixture to be processed and analyzed when it is outside or inside the apparatus. If the reaction device is not already in the apparatus, the reaction device will be inserted into the apparatus after filling, in order to carry out the chemical reaction and analyze the reaction product.

The present invention will be explained in more detail below with the aid of the nonlimiting drawings, in which.

The present invention relates to a reaction device, comprising a sample chamber matrix (1) containing at least two reaction chambers (2), of which the top faces and the side walls facing a light source (24, 25) or a neighboring reaction chamber are transmissive for electromagnetic radiation in a range necessary for fluorescence measurement; and at least one opening (3). According to one embodiment of the present invention, the light sources are selected so that they emit electromagnetic radiation with a wavelength of from 400 nm inclusive to 700 nm inclusive. According to another embodiment of the present invention, lasers that emit electromagnetic radiation suitable for the excitation of fluorescence emission are used as light sources.

The reaction device according to the present invention provides a multichamber system, which readily makes it possible to simultaneously carry out chemical reactions in a plurality of chambers and detect the chamber contents of a plurality of chambers. This is achieved according to the invention in that the top faces of the reaction chambers and their side walls facing a light source or a neighboring reaction chamber are transmissive for electromagnetic radiation in a range necessary for fluorescence measurement. The reaction chambers can be heated rapidly, in a controlled and precise way with the aid of the integrated heating instrument and/or temperature measuring instrument. The provision of an integrated cooing instrument (13) likewise allows rapid and precise cooling of the reaction device and the reaction mixtures.

The present invention furthermore concerns an apparatus for carrying out detection and detecting chemical reactions, comprising a) at least two light sources, which emit electromagnetic radiation in a range necessary for fluorescence measurement;

b) a detection unit for detecting electromagnetic radiation in a range necessary for fluorescence measurement, this unit being orthogonal to the at least two light sources;

c) a control unit comprising a central processing unit for controlling the temperature and the at least two light sources, as well as a signal processing unit for receiving and processing a signal from the detection unit;

d) an opening for accommodating the aforementioned reaction device, the reaction device lying in the plane of the at least two light sources and underneath the detection unit.

The arrangement and control of the optical system in the apparatus even make it possible to process and evaluate reaction mixtures with very small volumes.

This apparatus may, for example, be used to implement a method for carrying out a fluorometrically evaluatable reaction, involving the steps of a) preparing reaction mixtures, which contain fluorescent constituents or in which fluorescent constituents are formed in the course of the chemical reaction;

b) carrying out the chemical reaction by setting at least one reaction temperature in the reaction mixtures;

c) exciting the reaction mixtures using electromagnetic radiation in a range necessary for fluorescence measurement;

d) fluorometric evaluation of the reaction mixtures by measuring the emitted fluorescent radiation;

characterized in that at least one reaction mixture is simultaneously excited using the electromagnetic radiation in step c), and the fluorescent radiation emitted by at least this one reaction mixture is detected and evaluated in step d).

This is achieved according to the invention in that the reaction mixtures are excited with electromagnetic radiation of differing intensity in step c), so that the intensity of the fluorescent radiation emitted by the reaction mixtures differs and the reaction mixtures can be selectively evaluated on the basis of differing signal intensity.

Another possible way of selectively evaluating the content of a reaction chamber according to the invention consists in selecting reaction mixtures with fluorescent constituents that emit fluorescent radiation at different frequencies, so that the reaction mixtures can be selectively evaluated on the basis of differing signal frequency.

The explanations given below relate to the present invention in general, and are not restricted to the embodiments shown in the figures.

Figure 1:
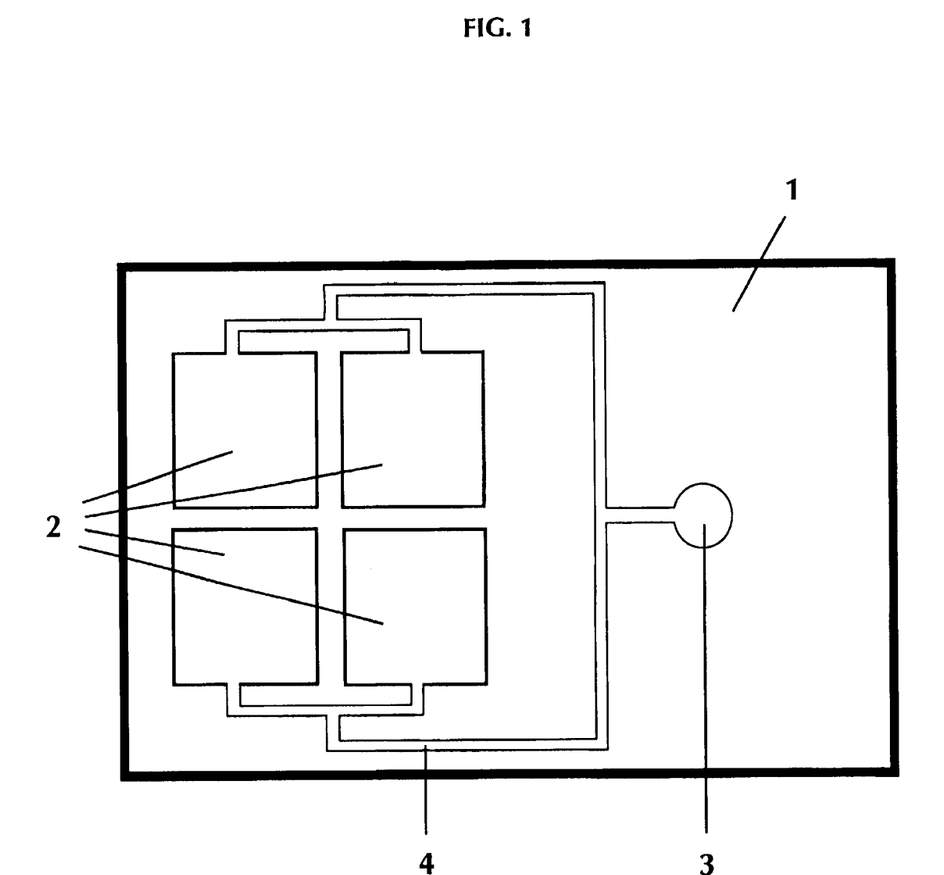
FIG. 1 shows a schematic view of an embodiment of the sample chamber matrix of the reaction device according to the invention.

FIG. 1 shows a schematic view of an embodiment of the sample chamber matrix of the reaction device according to the invention. The sample chamber matrix (1) comprises at least two reaction chambers (2). In the embodiment shown in FIG. 1, four reaction chambers (2) are provided in the sample chamber matrix (1). The maximum number of reaction chambers in the sample chamber matrix is limited only by the physical parameters of the system according to the invention (signal-to-noise ratio of the obtained signal, focusing of the incident and emitted light). According to the invention, it is preferable to provide from 2 to 16 reaction chambers (2), in particular at least three reaction chambers (2) in the sample chamber matrix (1), in order to allow a test sample, a positive sample and a negative sample to be processed and analyzed simultaneously. For reasons of production technology, a number of reaction chambers (2) which form a square array of reaction chambers (2), or a single row of reaction chambers (2), is furthermore preferable according to the invention.

The reaction device according to the present invention provides a multichamber system which allows straightforward detection of the chamber contents. This is achieved according to the invention in that the top faces of the reaction chambers (2) and their side walls facing a light source (24, 25) or a neighboring reaction chamber are transmissive for electromagnetic radiation in a range necessary for fluorescence measurement. According to the invention, it is therefore unnecessary to provide windows or holes in the walls of the reaction chambers (2), through which electromagnetic radiation can be sent in and let out. In this way, it is possible for the electromagnetic radiation emitted by a single light source to be passed through all the reaction chambers (2) arranged in a row relative to the light source. In the sample chamber matrix (1) shown in FIG. 1, the reaction chambers (2) are arranged in vertical and horizontal rows with respect to one another. The reaction chambers (2) are illuminated by two mutually orthogonal rows of light sources (2 each in the case of FIG. 1). With such arrangement, the individual reaction chambers (2) can be selectively illuminated as described below. A more detailed discussion of the light source arrangement and the detection will be given below with reference to FIG. 5.

Neighboring reaction chambers (2) in the sample chamber matrix (1) may be respectively connected to one another by a side wall. Since this side wall is transmissive for electromagnetic radiation in a range necessary for fluorescence measurement, as mentioned above, the electromagnetic radiation sent into the first chamber enters the subsequent second chamber through their common wall, when the neighboring chambers are arranged in a row relative to a light source. It is also possible according to the invention, however, for there to be a free space between neighboring reaction chambers (2) in the sample chamber matrix (1). In such a free space, instruments may be provided which modify, for example attenuate, or prevent the passage of incident light from the first chamber into the neighboring second chamber. Such an instrument may, for example, involve filters or air channels. It is also possible for an instrument by which the incident radiation is amplified to be provided in the free space. This may involve mirrors or prisms.

The sample chamber matrix (1) has a least one opening (3). The reaction chambers (2) may be filled or vented through this opening (3). The reaction chambers (2) are in communication with the opening (3) via channels (4), which are also located in the sample chamber matrix. It is possible to provide a plurality of openings (3), in order to allow either separate filling and venting of all the reaction chambers (2), or in order to fill and vent the reaction chambers (2) independently of one another.

In the arrangement shown in FIG. 1, all the reaction chambers (2) are connected to an opening (3) through channels (4). In order to allow separate filling and venting of the individual reaction chambers, regulators by which particular channels can be opened or closed may be provided in the channels (4).

The reaction chambers are preferably dimensioned in such a way that they can hold reaction mixtures with a volume in the range of from 100 nl inclusive to 2 µl inclusive.

According to the present invention, one or more reaction chambers (2) may already contain one or more chemical substances, before they are additionally filled with the reaction mixture to be processed and analyzed through the opening(s) (3). These are preferably dry chemical substances, for example solids or freeze-dried substances. With the aid of these additional substances, the reaction mixture to be processed and analyzed can be treated differently in various reaction chambers (2) so as to determine different parameters of the reaction mixture.

Figure 2:
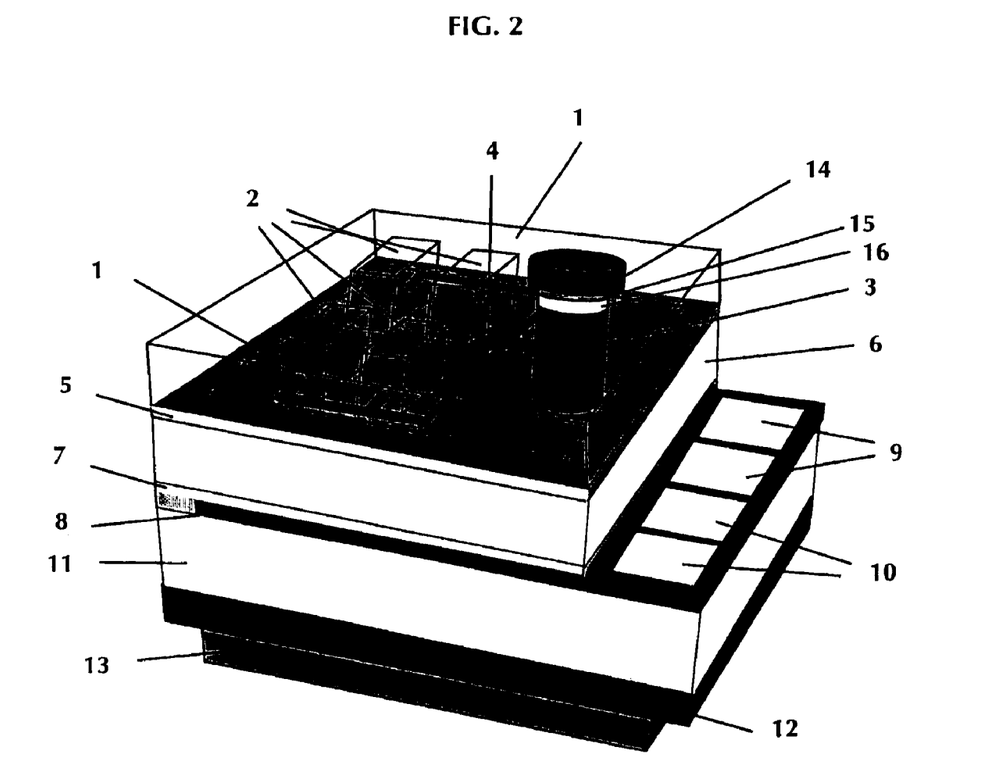
FIG. 2 shows a schematic side view of an embodiment of the reaction device according to the invention.

FIG. 2 shows a schematic side view of an embodiment of the reaction device according to the invention. In the embodiment shown in FIG. 2, a sample chamber matrix (1) having reaction chambers (2), an opening (3), and channels (4) for connecting the opening (3) to the reaction chambers (2), is formed in a body (1') which is transmissive for electromagnetic radiation in a range necessary for fluorescence measurement. This body (1') is preferably a shaped article made of glass. Other materials which are transmissive for electromagnetic radiation in a range necessary for fluorescence measurement, however, may also be used. Examples which may be mentioned include acrylic glass or polycarbonate. The reaction chambers (2), the opening (3), and channels (4) for connecting the opening (3) to the reaction chambers (2), are made in the body (1'). This procedure may be carried out in a conventional way known to the person skilled in the art. For example, the corresponding parts (2) to (4) may be made mechanically in the body (1'), for example by cutting. According to the invention, however, the parts (2) to (4) are preferably made chemically in the body (1') by etching. According to the present invention, the body (1') preferably has a thickness of 500-600 µm.

In the embodiment shown in FIG. 2, the reaction chambers (2) are made in such a way that there is a side wall consisting of the material of the body (1') between neighboring reaction chambers. As mentioned above, however, it is also possible to remove parts of the body (1') from the gap between neighboring reaction chambers (2), so as to provide a free space.

The body (1') with the sample chamber matrix (1) is connected via a thin layer (5) of a resilient synthetic compound, for example a rubber-like material such as silicone rubber, to a layer (6) of a thermally conductive material. The layer (6) should have a thermal conductivity which is as high as possible, since the heat generated in the heating layer (8) is transferred to the reaction chambers (2) via the layer.

The layer (6) preferably consists of silicon or thermally conductive silicon compounds. According to the present invention, the layer (6) preferably has a thickness of at most 500 µm. The layer (6) is connected via a thin layer (7) to a layer (11) of insulating material. The layer (7) bonds the layer (6) and the layer (11) without substantially affecting the thermal transfer inside the reaction device. The layer (7) consists of an adhesive. The exact composition of the layer (7) can be selected in a straightforward way by the person skilled in the art, according to his or her technical knowledge, with reference to the materials of the layers to be connected. In order to connect a layer (6) of silicon to a layer (11) of glass, for example, a UV-curable adhesive, for example an acrylate-based plastic, may be used as the material for the layer (7).

The heating layer (8) is used for heating the reaction chambers (2). The heating layer (8) will be explained in more detail below with reference to FIG. 3. It forms a heating instrument and/or temperature measuring instrument integrated in the reaction device. The reaction chambers (2) can be heated in a controlled and precise way with the aid of the integrated heating instrument and/or temperature measuring instrument. Not all of the reaction device is heated in this case, but merely the part lying above the integrated heating instrument and/or temperature measuring instrument. This allows significantly more rapid and precise heating of the reaction chambers (2), in comparison with conventional systems. The heating layer (8) is arranged on the surface of the layer (11). According to the invention, it is preferable for the layer (8) to be made of a metal, for example copper or a noble metal such as platinum. According to the present invention, the layer (8) preferably has a thickness of 500 nm-1 µm.

The contacts (9) of the heating instrument and the contacts (10) of the temperature measuring instrument are also arranged in the heating layer. The contacts are used to establish a connection from the reaction device to the control unit of the rest of the apparatus, when the reaction device has been inserted into the apparatus. FIG. 2 shows two of each these contacts (9) and (10). The present invention is not, however, restricted to this number of contacts. The type of contacts can be readily selected by the person skilled in the art with reference to the exact requirements. In many cases, for example, it may prove advantageous to design the contacts as contact springs.

As already mentioned, the heating layer (8) is formed partially by the surface of the layer (11). The layer (11) consists of a thermally insulating material, for example glass. This prevents the heat generated in the layer (8) from being transferred to regions of the reaction device other than the reaction chambers (2). According to the present invention, the layer (11) preferably has a thickness of 500 µm-2 mm.

The layer (11) is located on a support (12). This support (12) is made of a material conventionally used for these purposes.

A cooling instrument (13) for cooling the reaction device is arranged underneath the support (12). According to the invention, any cooling instrument (13) conventionally used for such applications may be employed. It is preferable to use a Peltier cooling element as the cooling instrument (13). The provision of an integrated cooling instrument (13) likewise allows rapid and precise cooling of the reaction device.

According to the invention, the at least one opening (3) is closed after filling with the reaction mixture, in order to prevent contamination of the reaction mixture. All known sealing systems are in principle suitable for this. FIG. 2 shows a closure lid (14). A block (15) is fitted on the lower side of the closure lid (14). This block (15) consists of a material with a thermal conductivity that is as low as possible. The reaction device is thereby thermally decoupled from the surroundings. Exact control of the temperature in the reaction chambers (2) can be ensured in this way. A layer (16) for sealing the opening (3) is fitted on the surface of the block (15) facing toward the opening (3). This layer (15) may be made of any conventional sealing material, for example rubber. It must ensure that no liquid or no gas can escape from the reaction chambers (2), even at elevated temperatures.

Figure 3:
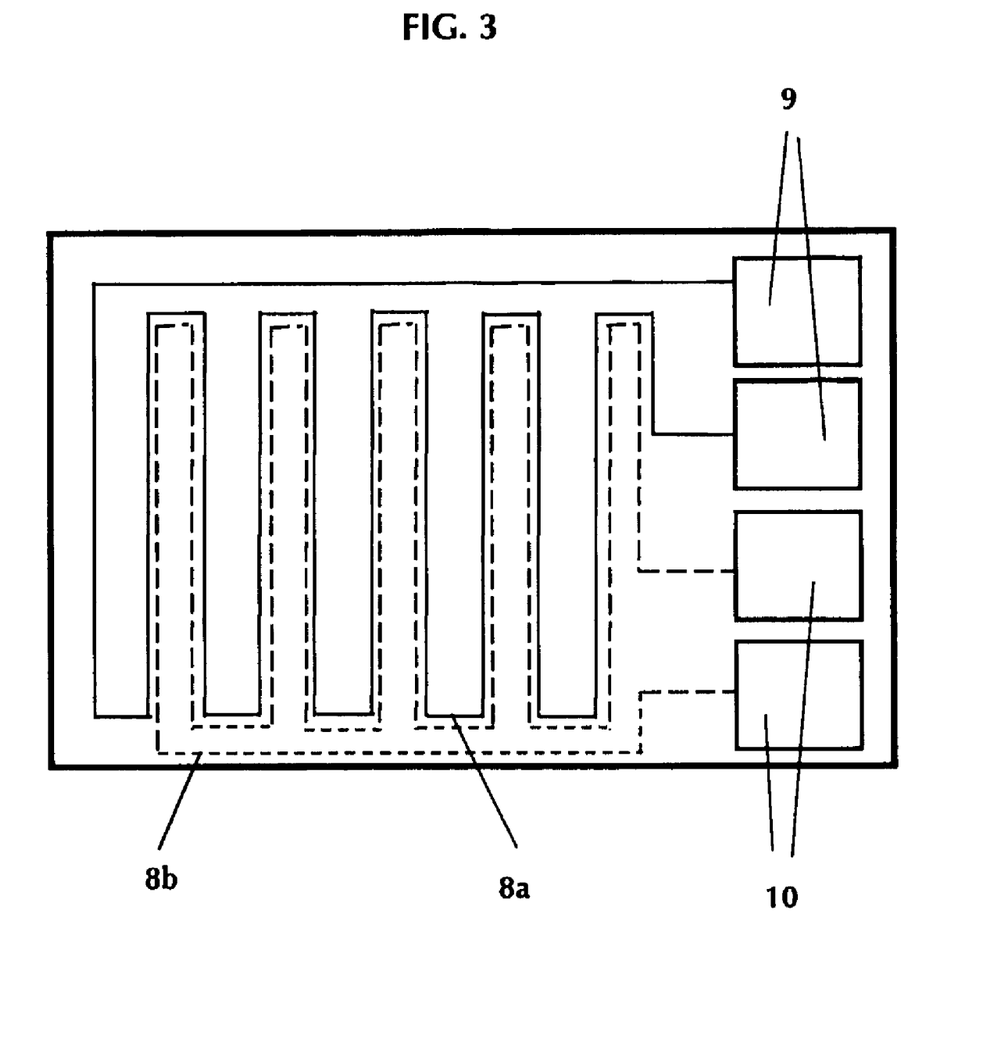
FIG. 3 shows a schematic view of an embodiment of the heating instrument and the temperature measuring instrument of the reaction device according to the invention.

FIG. 3 shows a schematic view of an embodiment of the heating instrument (8a) and the temperature measuring instrument (8b) of the reaction device according to the invention. The heating instrument (8a) and the temperature measuring instrument (8b) are arranged in the heating layer (8), as mentioned above. According to the invention, it is preferable for the heating instrument (8a) and the temperature measuring instrument (8b) each to be designed as resistors. They are arranged in the form of looped conductive tracks on or in the heating layer (8). If the heating instrument (8a) is a heating resistor, it should be made of a material with a resistance that is as low as possible. On the other hand, when it is designed as a resistor, the temperature measurement device (8b) should be made of a material with a resistance that is as high as possible. These conductive tracks are preferably made of a metal, for example copper or a noble metal such as platinum. It is particularly preferable for the heating instrument (8a) and the temperature measuring instrument (8b) to be made of the same material, for example copper or a noble metal such as platinum. This is preferred for technical production reasons. In this case, the material that is used represents a compromise between the various requirements mentioned above. The heating instrument (8a) and the temperature measuring instrument (8b) may be formed in the heating layer (8) by conventional methods, for example etching. The conductive tracks which respectively form the heating instrument (8a) and the temperature measuring instrument (8b) terminate in the respective contacts (9) and (10). When the reaction device has been inserted into the rest of the apparatus, the heating instrument (8a) and the temperature measuring instrument (8b) are respectively connected to the control unit via the contacts (9) and (10).

According to the present invention, it is moreover conceivable in principle to provide a reaction device in which different parts of the reaction device are driven by a separate heating instrument. This allows selective and controlled heating of individual parts of the reaction device.

According to the present invention, the reaction device may contain coding. This coding contains the information as to whether and for which chemical reaction, or target, the reaction device is specifically provided. This is expedient, for example, when additional chemical substances are provided in the reaction chambers.

The reaction device may be produced according to conventional methods known to the person skilled in the art.

Figure 4:
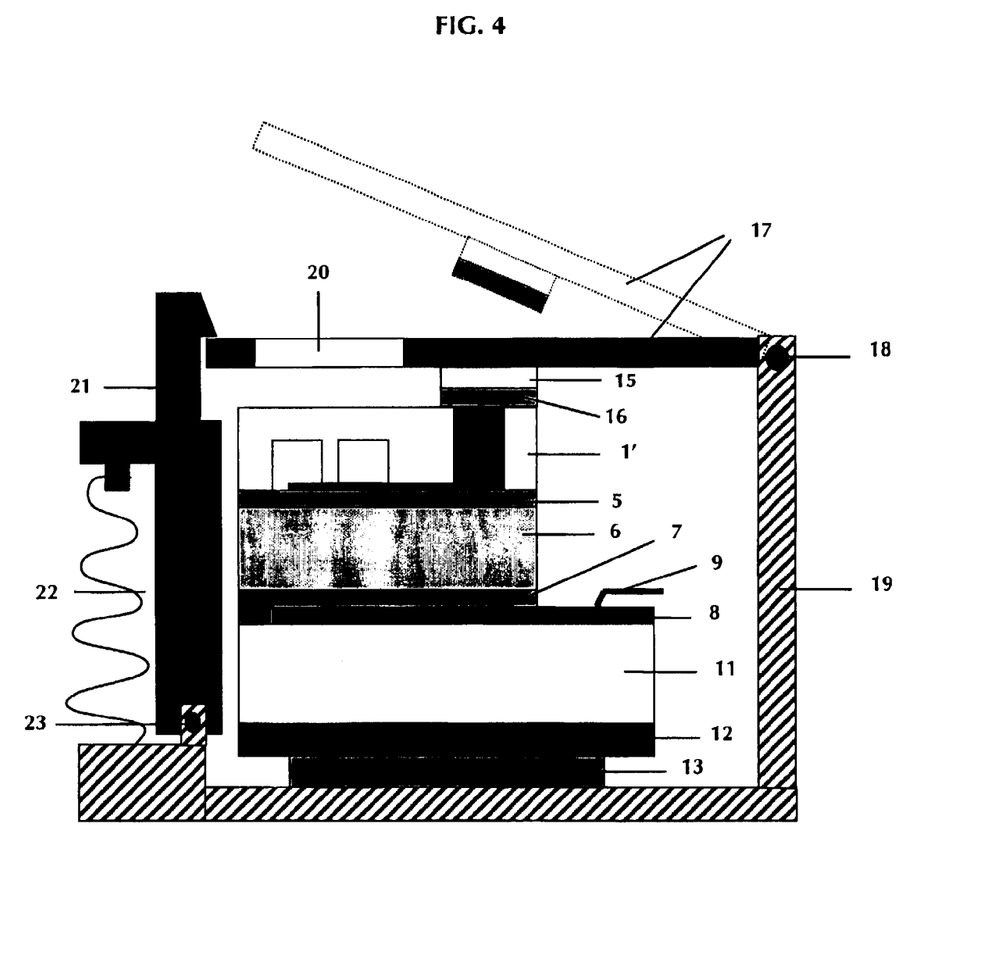
FIG. 4 shows a schematic side view of an embodiment of the reaction device according to the invention in a housing.

FIG. 4 shows an inventive embodiment of the reaction device in which the reaction device is arranged in a housing (19). The housing (19) is connected to a closure lid (17) via a hinge (18). The aforementioned block (15) and the sealing layer (16) are fastened on the lower side of the closure lid (17). When the closure lid (17) is shut, the opening (4) of the sample chamber matrix (1) is closed by the block (15) and the sealing layer (16). The closure lid (17) furthermore contains a window made of a material which is transmissive for electromagnetic radiation in a range necessary for fluorescence measurement, or an opening (20). When the closure lid (17) is shut, the window or the opening (20) lies directly above the reaction chambers (2). Electromagnetic radiation from the reaction chambers (2) can therefore shine through the window or the opening (20) into a detection unit lying above the window or the opening (20).

The closure lid (17) may be fixed by the frame (21). The fixing may be carried out in any way conventionally used for this. In FIG. 4, for example, the frame (21) is movably mounted in the hinge (23). The frame (21) is kept under tension by means of a spring (22). This tension fixes the closure lid (17) when it is pressed under the frame (21).

The reaction device is in communication with the housing (19) via the cooling instrument (13). In this way, heat generated in the reaction device can be dissipated to the housing (19) via the cooling instrument (13).

Figure 5:
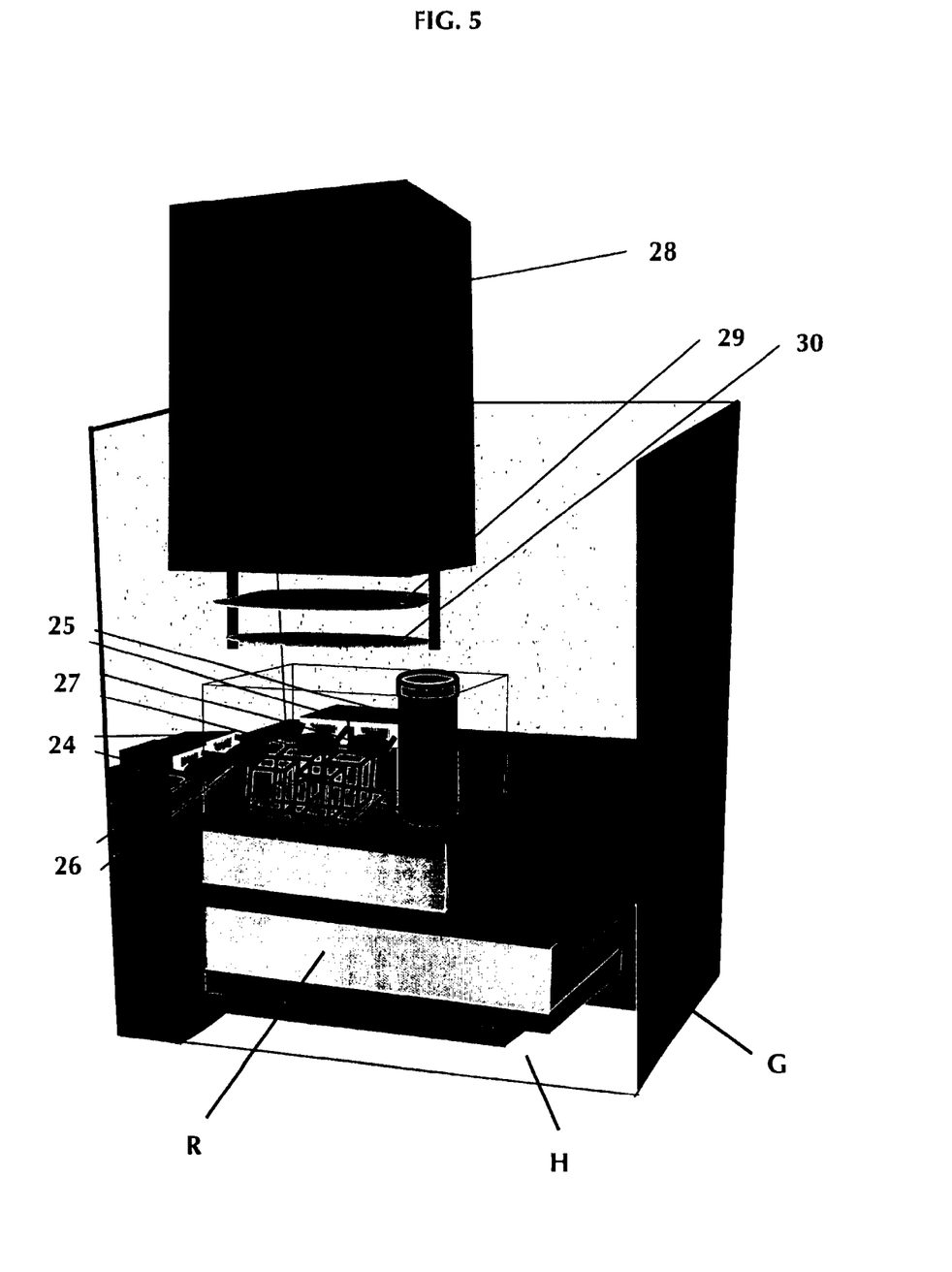
FIG. 5 shows a schematic view of an embodiment of the apparatus according to the invention.

FIG. 5 shows a schematic image of an embodiment of the apparatus according to the invention for carrying out and evaluating chemical reactions. The device has an opening (H) for accommodating the aforementioned reaction device. In FIG. 5, the reaction device has been inserted into this opening (H). In this embodiment, the reaction device is filled with the reaction mixture to be processed and analyzed outside the apparatus, and subsequently inserted into the apparatus. As can be seen in FIG. 5, when it has been inserted, the reaction device is arranged in such a way that the light sources (24, 25) of the apparatus lie in the same plane as the reaction chambers (2). As described above, a row of reaction chambers (2) that form a line with the corresponding light source (24, 25) can be addressed by a light source (24, 25). With an array of reaction chambers (2), such as the array of 4 reaction chambers (2) shown in FIG. 5, two rows of light sources (24) and (25) are provided according to the invention. These rows of light sources (24) and (25) are mutually orthogonal, so that each reaction chamber (2) lies at the intersection of the radiation from two mutually orthogonal light sources (24) and (25).

The reaction chamber (2) lying at the intersection of the radiation from two activated light sources (24, 25) is in each case selected for the corresponding analysis procedure. In principle, however, the other reaction chambers (2) likewise lying in the radiation region of the light sources (24, 25) will also be illuminated. These other reaction chambers (2) may then likewise be excited to emit fluorescent radiation. The detection unit (28) in this case detects the fluorescent radiation emitted by all the excited reaction mixtures. The fluorescent radiation emitted by the reaction mixtures, however, differs with respect to intensity. When the radiation emitted by the light sources (24, 25) travels through the first reaction chamber lying in the radiation path, it experiences an attenuation (damping) because of interactions with the content of the reaction chamber (2). Further attenuation (damping) of the excitatory radiation from the light sources (24, 25) takes place when crossing through the connecting wall to the next neighboring reaction chamber (2). This attenuation may be further increased if, in one embodiment of the present invention, a free space in which air or a filter are arranged, for example, is provided between the neighboring reaction chambers (2).

The signals of different intensity received by the detection unit (28) can be separated from one another during the computational evaluation. If n reaction chambers (2) are arranged in a sample chamber matrix (1), and there are two mutually orthogonal rows of light sources (24, 25) at the edges of the sample chamber matrix (1), with the number of light sources being j and k, and with n=j*k, the excitation of the reaction chambers (2) can be controlled in such a way that each reaction chamber (2) is simultaneously excited only once by two light sources (24, 25). A measurement value is recorded by the detection unit (28) for each illumination. The detection unit (28) in this case records the sum of all the signals of the excited reaction chambers (2), the signal of the reaction chamber (2) lying at the intersection of the beam paths of the light sources (24, 25) being the strongest. As described above, it should be remembered that some of the radiation from the light sources (24, 25) will be absorbed by reaction chambers lying closer to the light source (24, 25) in the beam path and/or by the side walls. The signals from the reaction chambers (2) will be commensurately smaller when they are further away from the light source (24, 25). On the basis of these assumptions, a linear system of equations can be set up for all the reaction chambers (2) and signals, and the signal intensity of each individual reaction chamber (3) can be calculated therefrom.

For a sample matrix chamber (1) having 3*3 reaction chambers (2), that is to say with three rows of 3 reaction chambers (2) each, let light sources (24) be arranged at the edge in the line h and, orthogonally thereto, light sources (25) in the column v. If only the light source j in the line h and the light source k in the column v are activated, the reaction chambers produce the total signal $s_{jk}$. In this case (1−a) is the absorption coefficient for the reaction chambers arranged in the 2nd row and (1−b) is the absorption coefficient for the chambers arranged in the third row. This leads to a set of 9 equations of the type:

$$x_{j1}+ax_{j2}+bx_{j3}+x_{1k}+ax_{2k}+bx_{3k}=s_{jk}$$

....

The nine equations can be expressed as follows:

$$\underline{A}*\underline{x}=\underline{s}$$

Multiplication by the inverse of the matrix A on both sides of the equation makes it possible to calculate the signal intensity x of each individual reaction chamber (2). Selective evaluation of a particular reaction mixture in a particular reaction chamber (2) is therefore possible.

Selective evaluation of a particular reaction mixture in a particular reaction chamber (2) is, however, also possible if the reaction mixtures in the various reaction chambers (2) contain constituents that emit fluorescent radiation with differing frequency. When exposed to electromagnetic radiation with a defined frequency, only one of the plurality of reaction mixtures will therefore be excited to emit fluorescent radiation.

Another method according to the invention for selective evaluation of a particular reaction mixture in a particular reaction chamber (2) consists in preventing the emission of fluorescent radiation in one or more reaction chambers (2) by fluorescence quenching. This may be done, for example, by adding substances to which the excitatory energy taken up by the fluorescent constituents of the reaction mixture is transferred because of collision effects, without the emission of fluorescent radiation taking place.

According to another embodiment of the present invention, the reaction device (R) comprises a sample chamber matrix (1) that contains only a single row of reaction chambers (2). In this case, according to the invention, it is preferable to provide a row of light sources (24) corresponding to the row of reaction chambers. In this embodiment, each reaction chamber (2) is hence assigned a single light source (24). For a row consisting of three reaction chambers (2), a row of three light sources (24) will therefore be provided. The rows of reaction chambers (2) and light sources (24) are arranged mutually parallel, with each particular reaction chamber (2) lying in the beam path of only a single light source (24). Activation of this particular light source (24) will therefore only lead to illumination of the reaction chamber (2) assigned to this light source (24). Selective analysis of the content of this reaction chamber (2) is therefore possible.

According to the invention, monochromatic light sources are preferably used as the light sources (24, 25), in particular light emitting diodes (LEDs) or lasers. Lasers are preferred owing to their advantageous optical properties (for example emission of light with a narrow spread of wavelengths). The number of light sources is dependent on the number of reaction chambers (2) in the reaction device, each reaction chamber (2) being irradiated by two light sources (24, 25) in the case of a reaction chamber array and each reaction chamber (2) preferably being irradiated by one light source (24, 25) in the case of a single row of reaction chambers (2). According to the invention, for example, the light sources are selected in such a way that they emit electromagnetic radiation with a wavelength of from 400 nm inclusive to 700 nm inclusive. In principle, however, the excitation may also be carried out using electromagnetic radiation with a shorter wavelength. When lasers are used, for example, the radiation emitted by the light sources may even have wavelengths of, for example, 200 nm.

Filters (26, 27) may be arranged in the line between the light sources (24, 25) and the reaction chambers (2), in order to deliberately select and adjust the electromagnetic radiation incident in the reaction chambers (2). They are preferably bandpass filters, for example interference filters, which only allow electromagnetic radiation with particular wavelengths to reach the reaction chambers (2). According to the invention, the filters (26, 27) are preferably designed in such a way that they only transmit electromagnetic radiation that has a different frequency than the fluorescent radiation emitted by the reaction mixtures. This avoids radiation from the light sources with the same frequency as the fluorescent radiation emitted by the reaction mixtures inadvertently reaching the detection unit (28) and being evaluated there as a signal.

When the reaction device has been inserted into the apparatus, the reaction chambers (2) lie directly underneath a detection unit (28). The detection unit (28) is therefore arranged above the light sources (24, 25) and orthogonally to each of them. The electromagnetic radiation emitted by the light sources (24, 25) does not therefore reach the detection unit (28). The latter only picks up the electromagnetic radiation emitted by the reaction chambers (2).

According to the invention, the detection unit (28) is preferably a photon counter module. It is, however, also possible for other detector systems employed in fluorescence measurement to be used.

A lens (29) is preferably arranged between the detection unit and the reaction chambers (2). It is used to focus the radiation emitted by the reaction chambers (2) onto the detection unit (28).

One or more filters (30) may likewise be arranged in the line between the detection unit (28) and the reaction chambers (2), in order to deliberately select and selectively evaluate the electromagnetic radiation emitted from the reaction chambers (2). They are preferably bandpass filters, for example interference filters, which only allow electromagnetic radiation with particular wavelengths to reach the detection unit (28). According to the invention, the filter (30) is preferably designed in such a way that it only transmits electromagnetic radiation that has a different frequency than the radiation emitted by the light sources (24, 25). This avoids radiation from the light sources inadvertently reaching the detection unit (28) directly, and being evaluated there as a signal.

The device according to the invention furthermore comprises a control unit. This comprises a central processing unit, for example a microprocessor, by which the light sources (24, 25) are activated and the heating instrument (8a) and the temperature measuring instrument (8b) are controlled. The apparatus furthermore comprises a signal processing unit, by which the signals sent from the detection unit (28) are recorded and processed. The incoming signals in the central processing unit and/or signal processing unit, and the outgoing signals from the central processing unit, are optionally modified outside the central processing unit in units for amplification or modulation of signals, for example measurement amplifiers, power amplifiers or digitization units, respectively before entering the central processing unit and after leaving the central processing unit. The control unit furthermore contains software for the system operation. This software may, for example, be selected according to the procedures to be carried out with the system.

The control unit is preferably in communication with the heating instrument (8a) and the temperature measuring instrument (8b) via the contacts (9, 10), when the reaction device is in the inserted position in the apparatus.

The temperature can therefore be regulated very rapidly and precisely in the apparatus according to the invention. The reaction chambers (29) can furthermore be selectively addressed by activating different light sources (24, 25). The arrangement and control of the optical system in the apparatus even make it possible to process and evaluate reaction mixtures with small volumes.

The control unit may also comprise an input device, for example a keypad or a keyboard, and/or a display device, for example a monitor or a liquid-crystal display. The apparatus according to the invention can be operated using these instruments. The control unit may moreover also contain one or more interfaces. The control unit may be connected to external equipment via these interfaces. For example, the control unit may be connected via a suitable interface to an external computer, by means of which the apparatus according to the invention can be operated. The control unit may moreover be connected via a suitable interface to a printer.

Figure 6:
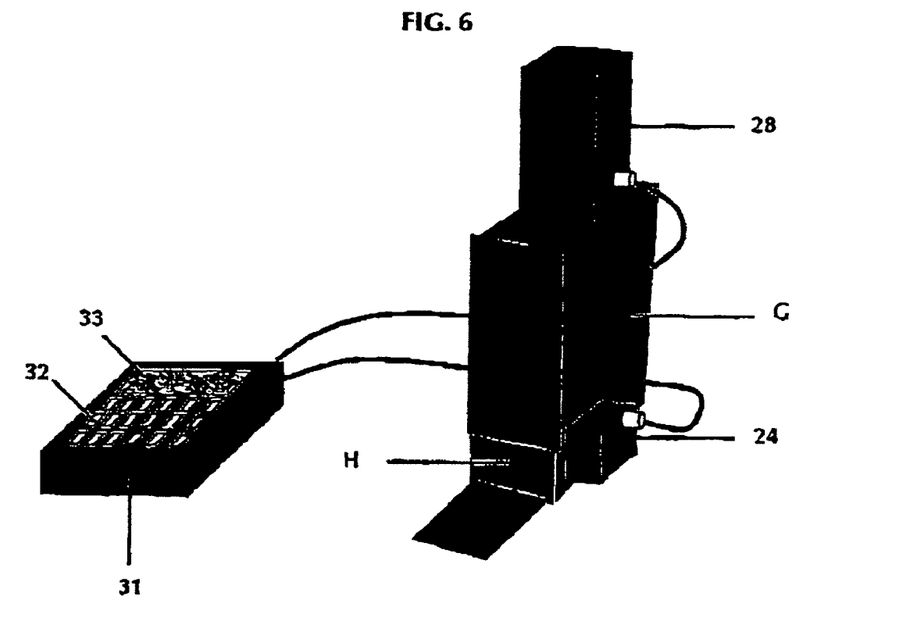
FIG. 6 shows a schematic view of the structure of an embodiment of the apparatus according to the invention.

The control unit may be arranged inside the apparatus according to the invention. Optionally, the control unit may moreover be provided outside the apparatus according to the invention. This embodiment is shown in FIG. 6. A controller (31) contains the control unit. The controller (31) also contains a keypad (32) and a display (33) for operation. The controller is connected, via a cable, to the apparatus into which the reaction device is inserted. The apparatus is constructed as described in FIG. 5.

Figure 7:
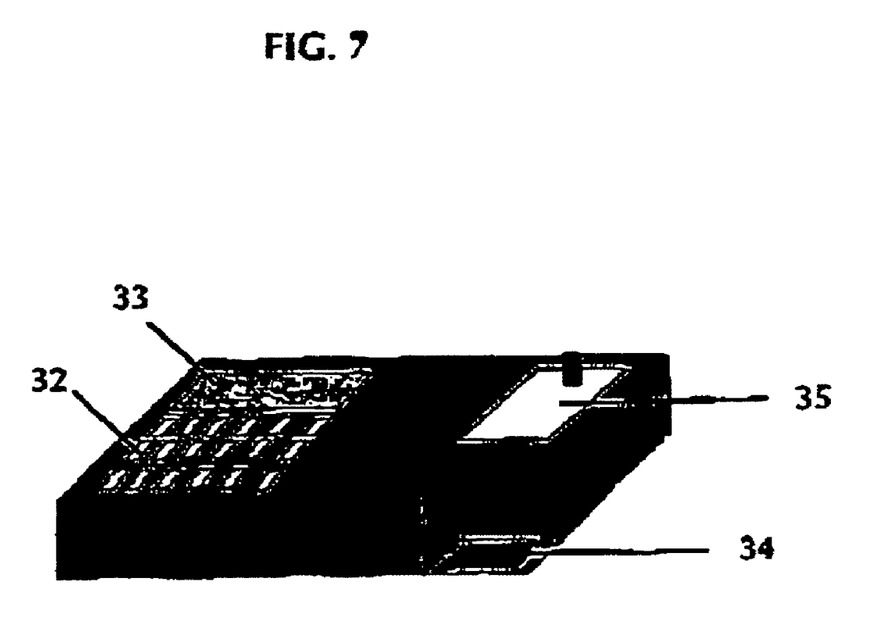
FIG. 7 shows a schematic view of the structure of another embodiment of the apparatus according to the invention.

Another embodiment of the system according to the invention is shown in FIG. 7. In this embodiment, the control unit is located inside the apparatus according to the invention. A keypad (32) and a display (33) for operation are provided. This, however, is only optional. As described above, the apparatus may likewise be connected via suitable interfaces to an external computer and/or an external printer. In this embodiment, the reaction device (R) is preferably located inside the device when filling with reaction mixture. The filling may be carried out through the accessible opening (34). The opening (34) is in communication with the reaction chambers of the reaction device (R) via channels (not shown). In other regards, the apparatus is constructed as described in FIG. 5. The procedure for carrying the chemical reaction and the subsequent evaluation is as described above. After it has been used once, the reaction device (R) can be removed through the opening (35) and cleaned or replaced.

The system according to the invention is based on a fluorescence measurement for the evaluation. In principle, however, other optical methods used for the evaluation of chemical reaction mixtures may be employed.

The reaction device according to the invention is in principle intended for single use. It may, however, also be cleaned and used repeatedly.

Chemical reactions can be performed and carried out with the system according to the invention. In particular, the system of the reaction device and the apparatus is suitable for carrying out chemical reactions in which it is necessary to execute controlled temperature cycles. An example of such a reaction is the polymerase chain reaction (PCR) described in the introduction. With the system according to the invention, it is possible both to evaluate the progress of the reaction by continual fluorescence measurement and to evaluate the obtained reaction product by fluorescence measurement.

The system according to the invention may furthermore be used exclusively for the detection of reaction mixtures. As explained above, a measurement of very small volumes can advantageously be carried out with the system according to the invention. It is therefore also advantageous to fill the reaction chambers of the reaction device with substances which can be fluorometrically detected without carrying out a chemical reaction, and to evaluate these using the system according to the invention.

In order to carry out a chemical reaction, the reaction device is firstly filled with the reaction mixtures to be processed and analyzed outside the rest of the apparatus. This is usually done by filling conventional syringes with the reaction mixture or mixtures to be processed and analyzed, and then injecting the syringe content into at least one opening (3). In principle, for example, pipettes, micropipettes or special cartridges or inkjet techniques are furthermore suitable for this. After filling, the at least one opening (3) is closed as described above and the reaction device is inserted into the apparatus.

The actual chemical reaction is carried out in the apparatus by using methods which are known to the person skilled in the art, and which are dependent on the reaction in question. In the case of PCR, a defined temperature cycle is executed several times in the apparatus, so that the reaction chambers (2) together with their content are brought to different temperatures for established periods of time. The temperature cycles, temperatures and periods of time to be used for PCR are known. In principle, PCR can be carried out in all its known variants with the aid of the system according to the invention. A preferred embodiment according to the present invention consists in heating a reaction mixture, containing the nucleic acid template to be amplified and analyzed, primers, polymerase, dNTPs and fluorescence probes to 90-100° C. for a particular period of time, followed by cooling, holding at a lower temperature, and reheating to 72° C. (depending on the polymerase being used), followed by denaturing at 90-100° C. As a rule, this temperature cycle needs to be carried out about 30-50 times, preferably about 35-40 times, before a sufficient amount of the intended DNA is available. While the reaction is being carried out, a fluorescence measurement as described below may be carried out in order to monitor the progress of the reaction.

A fluorescence measurement of the reaction mixture is subsequently carried out. To this end, the reaction mixture is subjected to a continuous temperature increase, for example at a heating rate of from 0.1° C./s to 10° C./s, while applying electromagnetic radiation with a wavelength suitable for the fluorescence measurement. Such measurement methods, and the way in which they are carried out, are known to the person skilled in the art.

The radiation emitted by the reaction mixture in the reaction chamber (2) is picked up by the detection unit and converted into an electrical signal. Optionally, after having first been modulated and/or amplified, this signal is sent to the control unit of the system, where it is evaluated using appropriate software. The evaluation of fluorometric measurements is known. According to the invention, the result of the fluorescence measurement is preferably output in the form of the first negative derivative ($-dF/dT$).

Even small volumes in the range of from 100 µl inclusive to 2 µl inclusive can be reliably processed and evaluated with the system according to the invention.

The conduct of a PCR with the system according to the invention will be illustrated with reference to a nonlimiting example.

EXAMPLE 1

The reaction chambers (2) were filled with two reaction mixtures through the opening (3) of the sample chamber matrix (1). One of the reaction mixtures contained small amounts of nucleic acids of the bacterium *Escherichia coli* (*E. coli*). The second reaction mixture contained small amounts of nucleic acids of the bacterium *Streptococcus pneumoniae*. The reaction chambers (2) were filled with the aid of conventional insulin syringes. The opening (3) was then closed and the reaction device was inserted into the apparatus. The temperature profile shown in FIG. 7 was applied to the reaction chambers (2). After the reaction mixtures had been heated to 95° C. for a period of 250 s, cooling was carried out to 48° C. After holding for 20 s at 48° C., heating was carried out again to 72° C. for 20 s, followed by heating to 95° C. for 5 s. This cycle was repeated about 30-45 times until a sufficient amount of bacterial DNA was formed in the reaction chambers (after 1-1.5 hours).

The fluorescence measurement was carried out during slow heating of the reaction mixtures contained in the reaction chambers. A decrease in the fluorescence occurred with increasing temperature. 50% of the probes are cleaved from the nucleic acid at the melting temperature. At this point, the first negative derivative (-dF/dT) of the measurement curve exhibits a maximum which is specific to a particular reaction mixture.

Figure 8:
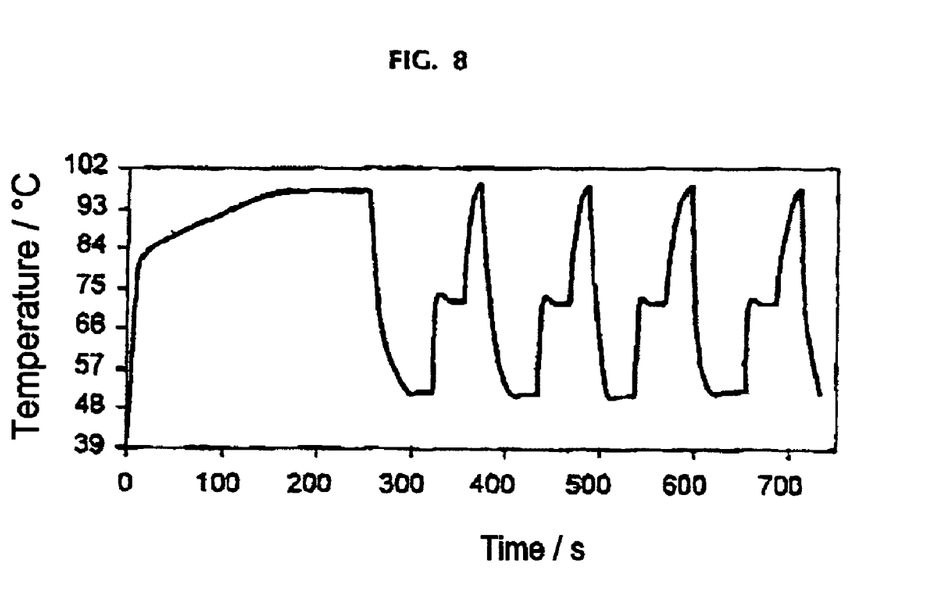
FIG. 8 shows the temperature cycle carried out in Example 1.
Figure 9:
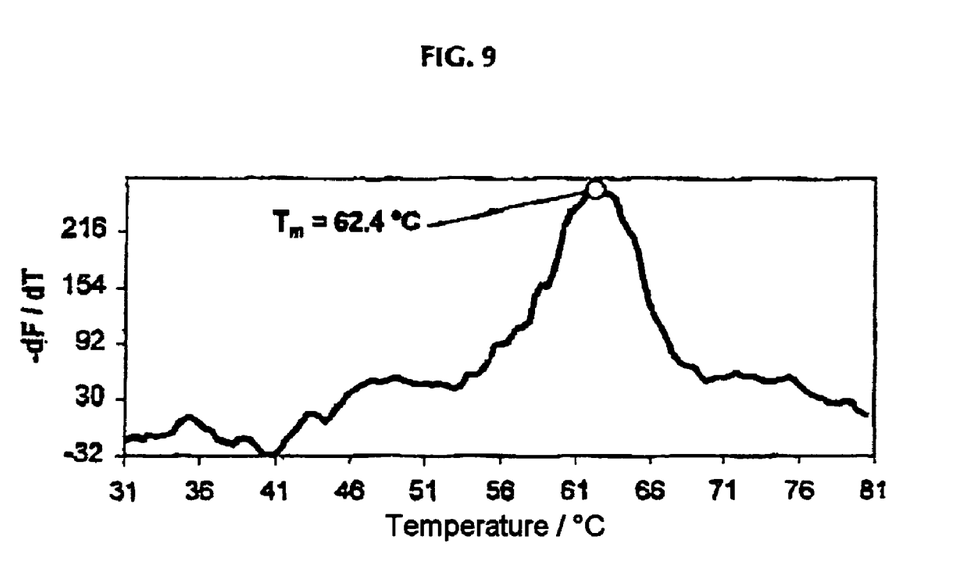
FIG. 9 shows the graph of the negative first derivative (−dF/DT) of the fluorescence measurement according to the Example 1 for the reaction mixture containing DNA of the bacterium *Escherichia coli*.
Figure 10:
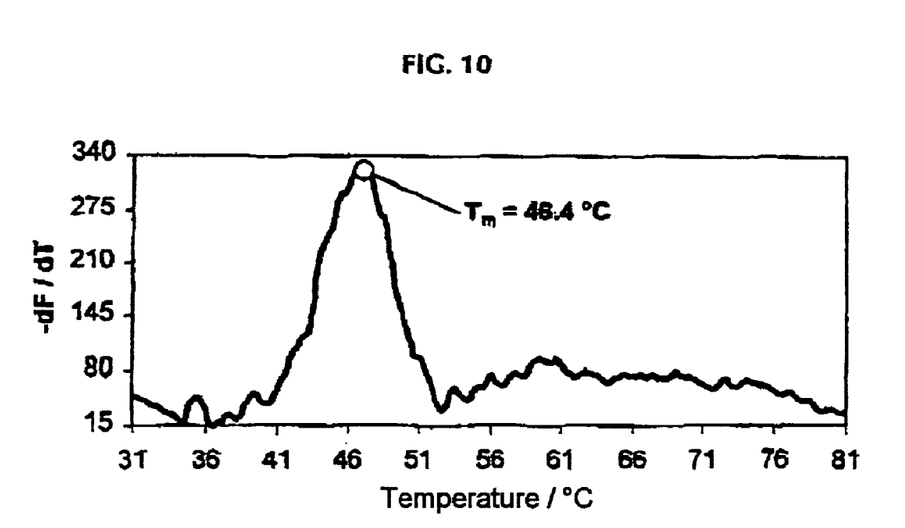
FIG. 10 shows the graph of the negative first derivative (−dF/DT) of the fluorescence measurement according to the Example 1 for the reaction mixture containing DNA of the bacterium *Streptococcus pneumoniae*.

FIGS. 8 and 9 show the respective negative first derivatives (-dF/DT) of the fluorescence measurement curves of the two reaction mixtures being studied. Characteristic maxima can respectively be seen for DNA of *E. coli* and *Streptococcus pneumoniae*.

With the system according to the invention, it is therefore possible to differentiate between different polynucleotides (DNA or RNA) contained in a reaction mixture. It is likewise possible to detect different mutations in polynucleotides with the system according to the invention. The system according to the invention can therefore be used to detect bacteria, viruses or particular DNA mutations. Besides the diagnosis of diseases or predispositions to diseases, the system according to the invention can therefore also be used for the field of pharmacogenomics, that is to say therapy designed individually according to the patient's genetic predisposition, or for phytochemistry, veterinary medicine, veterinary biochemistry, microbiology or in general for fields in which polynucleotide analysis needs to be conducted.

The invention claimed is:

1. A reaction device, comprising a sample chamber matrix containing a plurality of reaction chambers arranged in plural rows and columns,
    each of said reaction chambers having top faces and side walls that are transmissive for electromagnetic radiation in a range necessary for fluorescence measurement,
    at least one opening,
    plural light sources arranged in orthogonal rows corresponding to said reaction chambers, and
    a detection unit for detecting fluorescent radiation emitted from said reaction chambers as they are illuminated by said light sources, whereby said light sources can be activated in sequence and said detection unit can detect said emitted responsive fluorescent radiation and produce a signal which can be analyzed to determine the radiation emitted by each of said chambers.

2. The reaction device according to claim 1, wherein said device also comprises a heating instrument and/or a temperature measuring instrument.

3. The reaction device according to claim 2, wherein a layer of thermally conductive material is arranged between said heating instrument and said sample chamber matrix.

4. The reaction device according to claim 3, wherein said thermally conductive material is selected from the group consisting of silicon and thermally conductive silicon compounds.

5. The reaction device according to claim 2, wherein said heating instrument is a heating resistor.

6. The reaction device according to claim 5, wherein said heating resistor is made of a metal.

7. The reaction device according to claim 5, wherein said heating resistor is made of a metal from the group consisting of copper or a noble metal.

8. The reaction device according to claim 2, wherein said temperature measuring instrument is a temperature measurement resistor.

9. The reaction device according to claim 8, wherein said temperature measurement resistor is made of the same material as the heating resistor.

10. The reaction device according to claim 8, wherein said temperature measurement resistor is made of copper.

11. The reaction device according to claim 1, wherein said sample chamber matrix is formed in a body, which is transmissive for electromagnetic radiation in a range necessary for fluorescence measurement.

12. The reaction device according to claim 11, wherein said sample chamber matrix is etched into said body.

13. The reaction device according to claim 1, wherein said at least one opening is connected to said reaction chambers.

14. The reaction device according to claim 1, wherein neighboring reaction chambers in said sample chamber matrix are respectively connected to one another by a side wall.

15. The reaction device according to claim 1, wherein there is a free space between neighboring reaction chambers in said sample chamber matrix.

16. The reaction device according to claim 1, wherein one or more reaction chambers contain one or more chemical substances.

17. The reaction device according to claim 1, wherein said device furthermore comprises a cooling instrument, or a Peltier cooling element.

18. The reaction device according to claim 17, wherein said cooling instrument is arranged underneath a support.

19. The reaction device according to claim 18, wherein a layer of a thermally insulating material is arranged between the heating instrument and the support.

20. The reaction device according to claim 19, wherein said thermally insulating material is glass.

21. The reaction device according to claim 19, wherein said device furthermore comprises a closure means for said at least one opening.

22. The reaction device according to claim 21, wherein said closure means for said opening is connected to a cover of a housing which contains the reaction device, the cover having a window made of a material which is transmissive for electromagnetic radiation in a range necessary for fluorescence measurement or an opening in the region above the sample chamber matrix.

* * * * *